United States Patent [19]
Silva

[11] Patent Number: 5,611,686
[45] Date of Patent: Mar. 18, 1997

[54] PIN STABILIZER FOR DENTAL MODEL

[76] Inventor: Tyrone A. Silva, 5851 Holmberg Rd., Apt. 2923, Parkland, Fla. 33067

[21] Appl. No.: 406,164

[22] Filed: Mar. 17, 1995

[51] Int. Cl.⁶ .................... A61C 19/00; A61C 11/00
[52] U.S. Cl. .............................. 433/74; 433/60
[58] Field of Search .................... 433/53, 54, 60, 433/65, 66, 67, 74

[56] References Cited

U.S. PATENT DOCUMENTS

| | | | |
|---|---|---|---|
| 1,811,747 | 6/1931 | Coble | 433/65 X |
| 2,510,152 | 6/1950 | Stoll | 433/65 X |
| 2,550,043 | 4/1951 | De Lautour | 433/65 |
| 3,510,947 | 5/1970 | Tuccillo et al. | 433/60 |
| 4,030,197 | 6/1977 | Linch, II et al. | 433/60 |
| 4,319,875 | 3/1982 | Beckwith | 433/60 |
| 4,321,036 | 3/1982 | Weissman | 433/74 |
| 4,462,801 | 7/1984 | Lagios | 433/60 |
| 5,352,117 | 10/1994 | Silva | 433/60 |

FOREIGN PATENT DOCUMENTS

| | | |
|---|---|---|
| 494923 | 9/1919 | France. |
| 1456405 | 11/1976 | United Kingdom. |

*Primary Examiner*—Nicholas D. Lucchesi
*Attorney, Agent, or Firm*—Edward M. Livingston, Esq.

[57] ABSTRACT

A pin stabilizer fir dental models (14) has a plurality of positioning pins (1) extended from an articulator base plate (2) for insertion into positioning sleeves (3) that are cast in a dental model while the positioning pins are in the positioning sleeves. Quickly and easily then, the dental model can be attached repeatedly to and detached repeatedly from a dental articulator (15) to which the articulator base plate is affixed for work on a dental model. The positioning pins and the positioning sleeves can be made of materials which do not deform from repeated use. A plurality of dental models can be constructed to fit onto an articulator base plate that is attachable to a bottom and/or top articulator jaw (16) of known types and sizes of dental articulators.

13 Claims, 4 Drawing Sheets

5,611,686

PIN STABILIZER FOR DENTAL MODEL

BACKGROUND OF THE INVENTION

This invention relates to means for securing dental models to dental articulators. In particular, it relates to use of a plurality of pins in a base member for holding dental models with sleeves that fit onto the pins in the base member.

Previously, dental models have been attached to dental articulators with various devices that do not provide the stability and versatility of this invention. One example of a different means for attachment of dental models to dental articulators is described in U.S. Pat. No. 4,321,036, issued to Weissman on Mar. 23, 1982. The Weissman patent taught a type of multiple-part dowel pin which required tools for its assembly and disassembly for use. It was more complicated and time-consuming for attachment of dental models to dental articulators and detachment of the dental models from the dental articulators repeatedly than desirable for dental technicians. British Patent Number 1,456,405, issued to Daub on Nov. 24, 1976, described a dental articulator having a connector pin that enabled an upper part of the articulator to rotate relative to a bottom part. Beneficial as this rotational adjustability was, it did not provide a means for convenient and fast attachment of a dental model to a dental articulator and then for quick-and-easy removal and replacement of the dental model for structuring teeth and bite factors without deforming a means for attachment of the model to the articulator.

SUMMARY OF THE INVENTION

In light of problems that have existed and that continue to exist in this field, objectives of this invention are to provide a pin stabilizer for a dental model which:

- Allows quick-and-easy attachment of a dental model to and removal of a dental model from a dental articulator repeatedly by a dental technician without deformation of the attachment means;
- Can be built into a dental model reliably and conveniently when the mold is being formed;
- Provides a base attachment means on an articulator for use with the same convenience and reliability for a plurality of dental models; and
- Is economical to use.

This invention accomplishes the above and other objectives with a pin stabilizer for dental models having a plurality of positioning pins extended from an articulator base plate for insertion into positioning sleeves that are cast in a dental model while the positioning pins are in the positioning sleeves. Quickly and easily then, a dental model can be attached repeatedly to and detached repeatedly from a dental articulator to which the base plate is affixed for work on the dental model. The positioning pins and the positioning sleeves can be made of materials which do not deform from repeated use. A plurality of dental models can be constructed to fit onto an articulator base plate that is attachable to bottom and/or top articulator jaws of known types and sizes of dental articulators.

The above and other objects, features and advantages of the present invention will become apparent to those skilled in the art upon a reading of the following detailed description when taken in conjunction with the drawings wherein there is shown and described an illustrative embodiment of the invention.

BRIEF DESCRIPTION OF THE DRAWINGS

This invention is described by appended claims in relation to description of a preferred embodiment with reference to the following drawings which are described briefly as follows:

DESCRIPTION OF PREFERRED EMBODIMENTS

Figure 1:
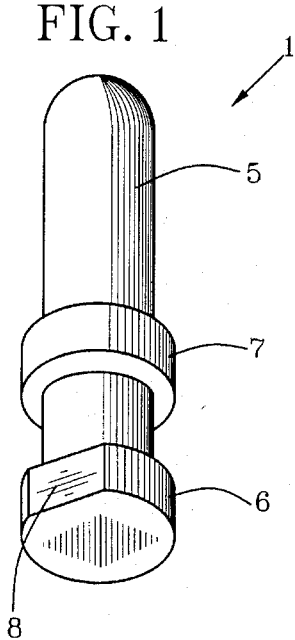
FIG. 1 is a perspective elevation view of a preferred type of positioning pin.
Figure 2:
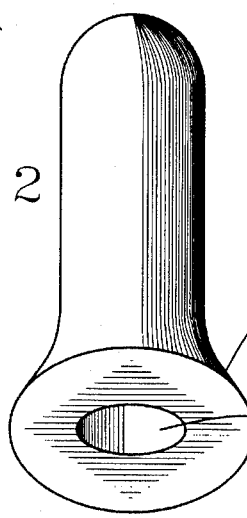
FIG. 2 is a perspective elevation view of a preferred type of positioning sleeve.
Figure 3:
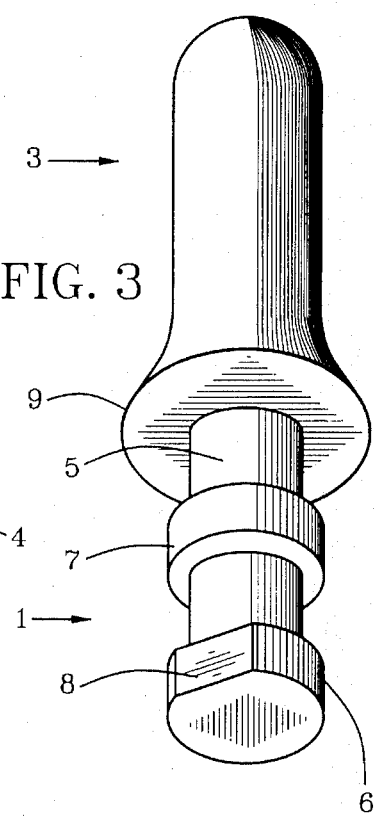
FIG. 3 is a perspective elevation view of an assembly of the FIG. 1 positioning pins and the FIG. 2 positioning sleeve.
Figure 4:
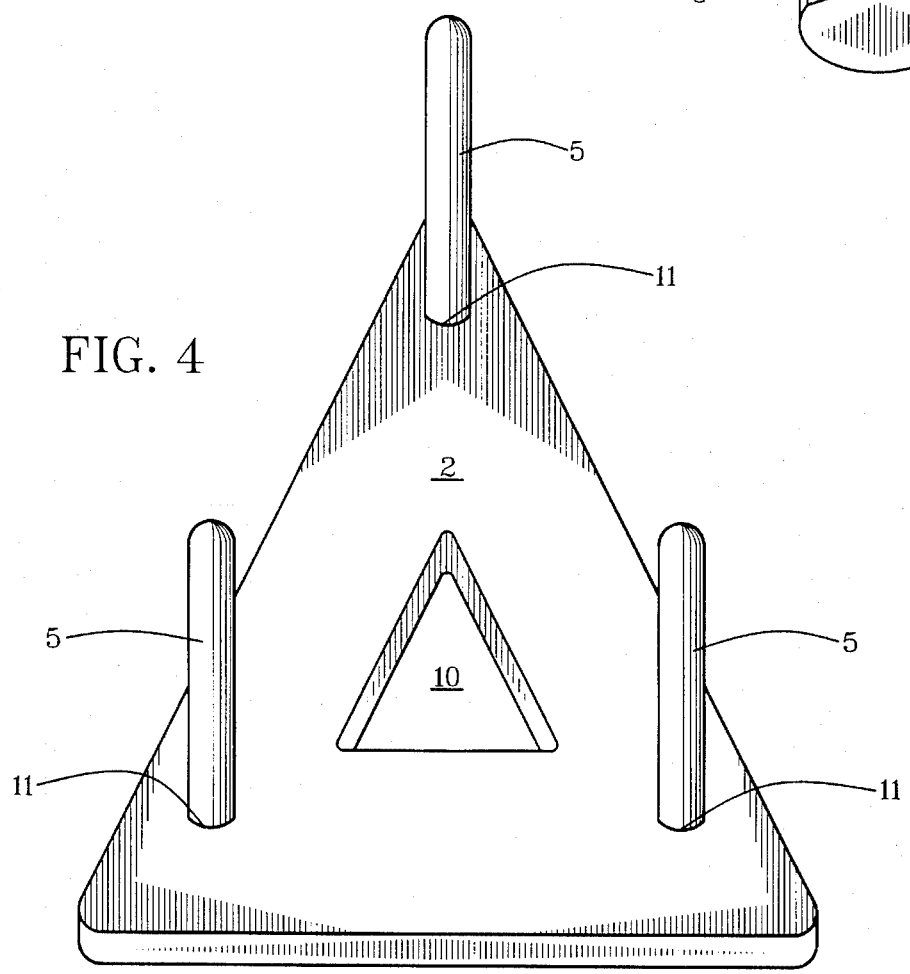
FIG. 4 is a perspective top view of an articulator base plate to which positioning pin are attached.
Figure 5:
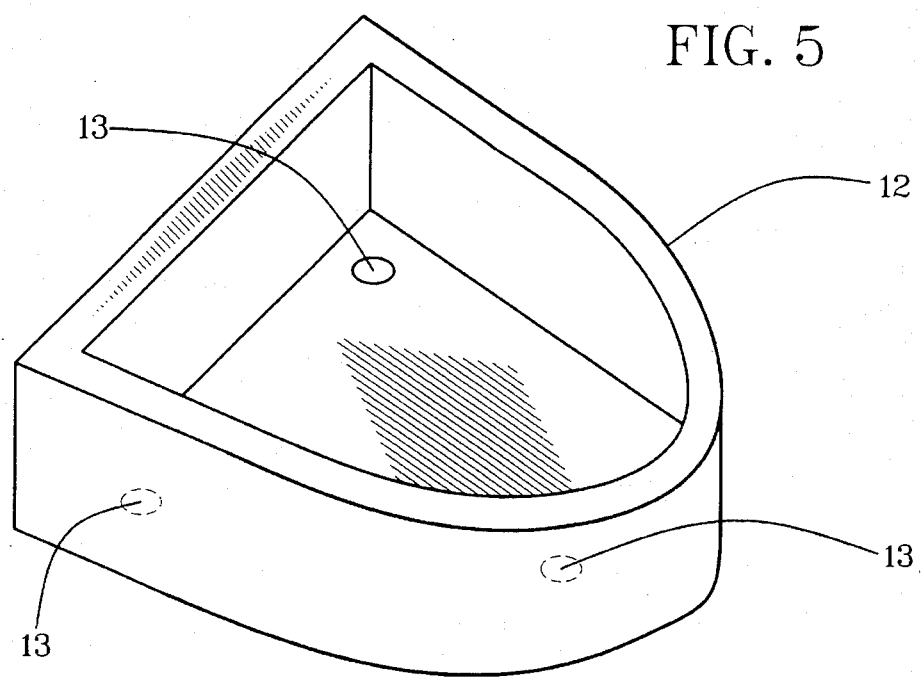
FIG. 5 is a perspective top view of a rubber mold with orifices for the positioning pins for casting dental models.
Figure 6:
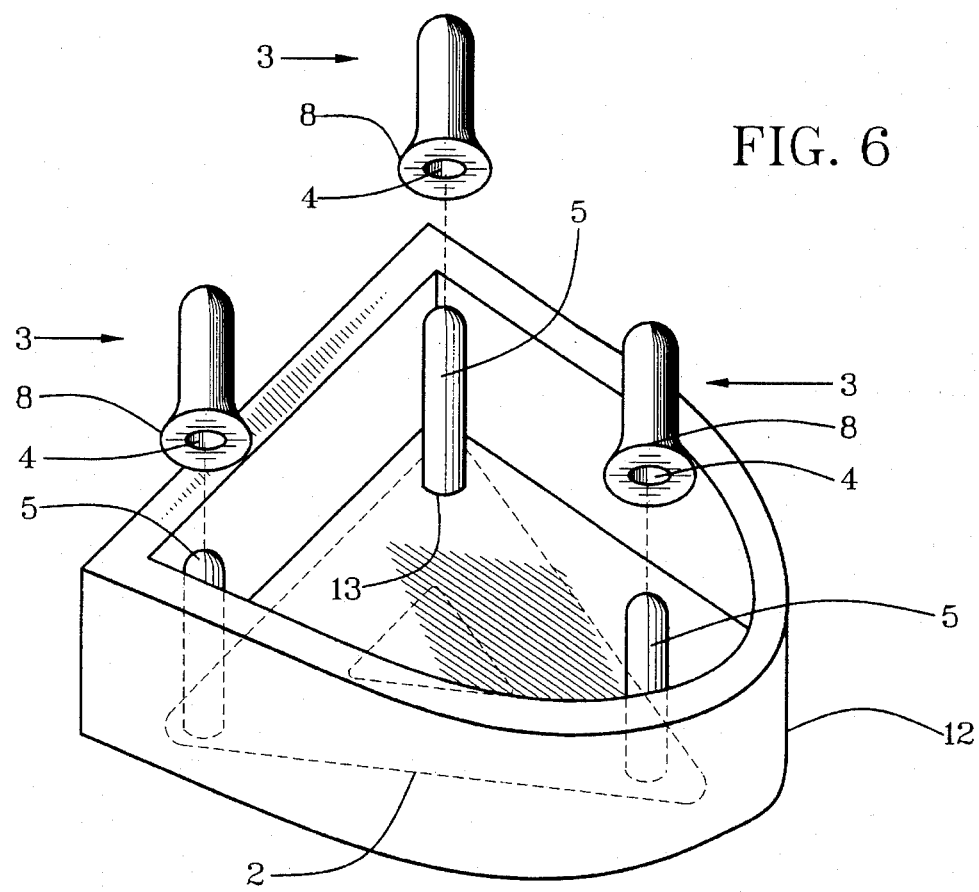
FIG. 6 is the FIG. 5 illustration with the positioning pins attached to the articulator base plate and inserted into mold orifices preparatory to casting a dental model in the mold.
Figure 7:
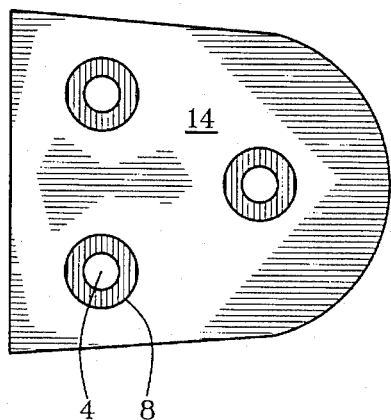
FIG. 7 is a bottom view of a dental model with the positioning sleeves cast into it.
Figure 8:
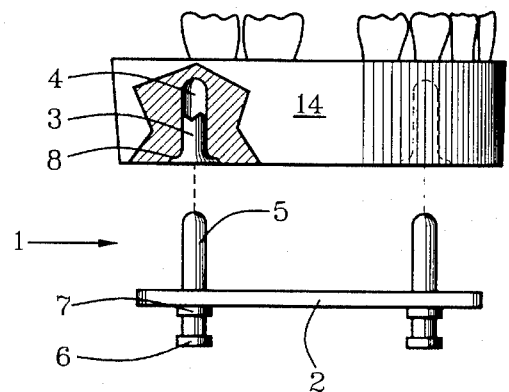
FIG. 8 is a side view of an assembly relationship of the positioning pins on an articulator base plate and positioning sleeves in a dental model that has been cast with the positioning sleeves in place.

Reference is made first to FIGS. 1–4. A plurality of positioning pins 1 are extended vertically from an articulator base plate 2. A plurality of positioning sleeves 3 have an internal periphery 4 that is sized and shaped to receive a pin shank 5 with designed snugness. A preferred form of the positioning pins 1 has a positioning-pin head 6 on a base end of each of the positioning pins 1 and a positioning-pin shoulder 7 at a designed distance from a positioning-pin head 6. The positioning-pin head 6 for this embodiment has a location flat 8. The positioning sleeves 3 have a sleeve flange 9 at an entry end. A preferred embodiment of the articulator base plate 2 is triangular with a triangular orifice 10 and three pin orifices 11 through which pin shanks 5 are inserted.

Referring to FIGS. 5–8, a rubber mold 12 for molding dental models has three mold orifices 13 through which three pin shanks 5 on an articulator base plate 2 are inserted.

Then a positioning sleeve 3 is positioned on each of the pin shanks 5. A dental model 14 is then cast in the rubber mold 12 with the positioning sleeves 3 in place on the pin shanks 5 of the positioning pins 1.

The dental model 14 is then removed from the rubber mold 12. Afterwards, the dental model 14 then can be removed from an assembly of the positioning pins 1 and articulator base plate 2 and repositioned on it without the rubber mold 12 as and when desired. Optionally, a plurality of different dental models 14 can be made in the same way with positioning sleeves 3 positioned on the pin shanks 5 of the positioning pins 1 when casting material such as plaster is placed in the rubber mold 12 for casting dental models 14. The same or different dental models 14 so constructed then can be replaced onto and removed from the positioning pins 1 as and when desired.

Figure 9:
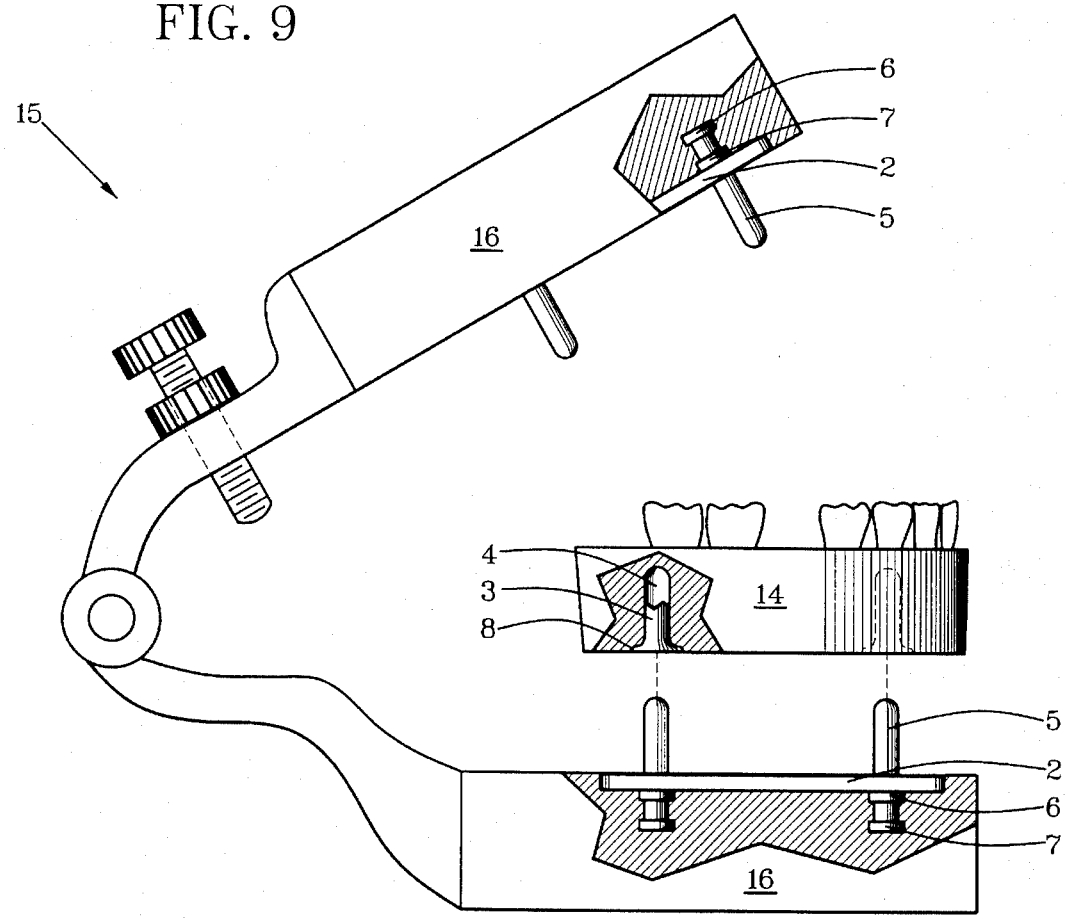
FIG. 9 is a partially cutaway side elevation view of a typical dental articulator showing assembly relationship of an articulator base plate and a dental articulator to which it is attached.

Referring to FIG. 9, the articulator base plate 2 with positioning pins 1 attached can be positioned on a dental articulator 15 by a preferred method of casting an articulator jaw 16 with positioning-pin heads 6 placed in jaw-casting material. Then the dental model 14 or other dental models constructed similarly can be positioned on and removed from the pin shanks 5 for placement on and removal from a dental articulator 15 as illustrated.

Figure 10:
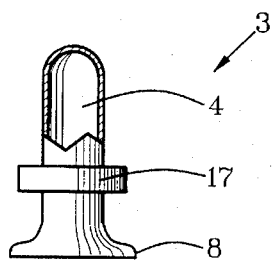
FIG. 10 is a partially cutaway elevation view of a positioning sleeve with a locator ring.
Figure 11:
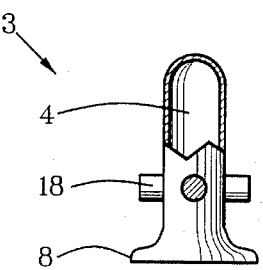
FIG. 11 is a partially cutaway elevation view of a positioning sleeve with a plurality of sleeve retainer members.

The positioning sleeve 3 can have a locator ring 17 shown in FIG. 10 or sleeve-retainer members 18 shown in FIG. 11 to hold the positioning sleeves 3 rigidly in dental models 14.

Figure 12:
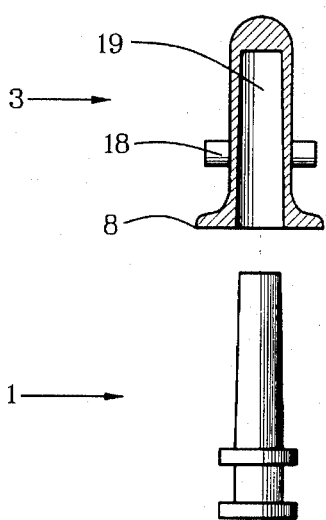
FIG. 12 is a side elevation view of a cutaway tapered positioning sleeve and a match-tapered positioning pin in assembly relationship.

As illustrated in FIG. 12, a positioning sleeve 3 can have a tapered internal periphery 19 and a positioning pin 1 can have a tapered external periphery 20 that is match-tapered to fit inside of the tapered internal periphery 19. This provides more rigid positioning of dental models 14 on dental articulators 15. Small-angle tapering provides more rigidity than large-angle tapering or no tapering. Also provided by small-angle tapering is convenient adherence from slight engagement pressure for holding a top dental model 14 in place until pulled from a top articulator jaw 16 to which it is attached. Accuracy of positioning a plurality of tapered internal peripheries 19 and tapered external peripheries 20 is provided by casting them in position as described above for un-tapered positioning pins 1 and positioning sleeves 3.

Figure 13:
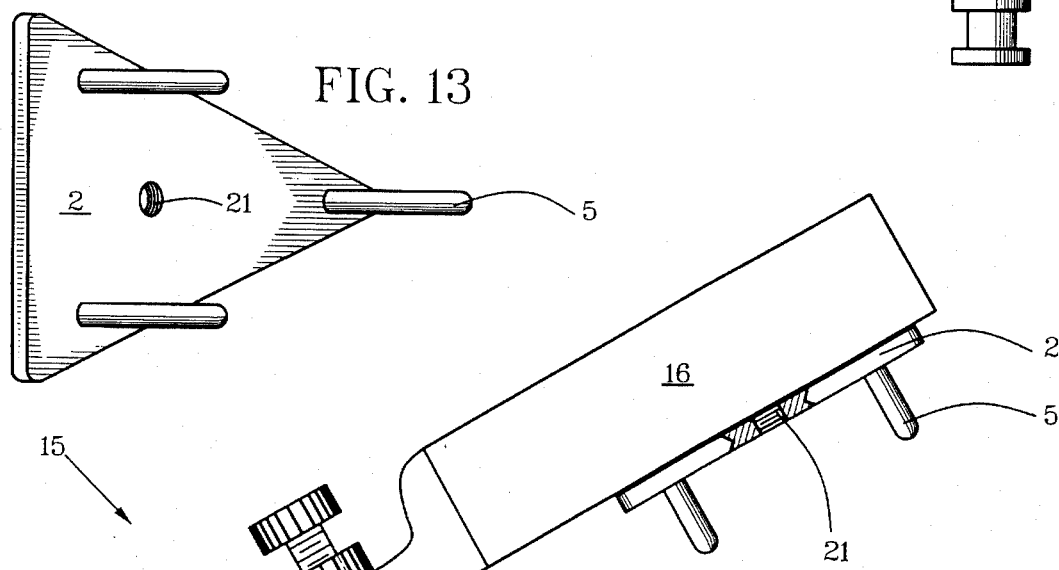
FIG. 13 is a perspective top view of an articulator base plate with a threaded base-plate fastener orifice.
Figure 14:
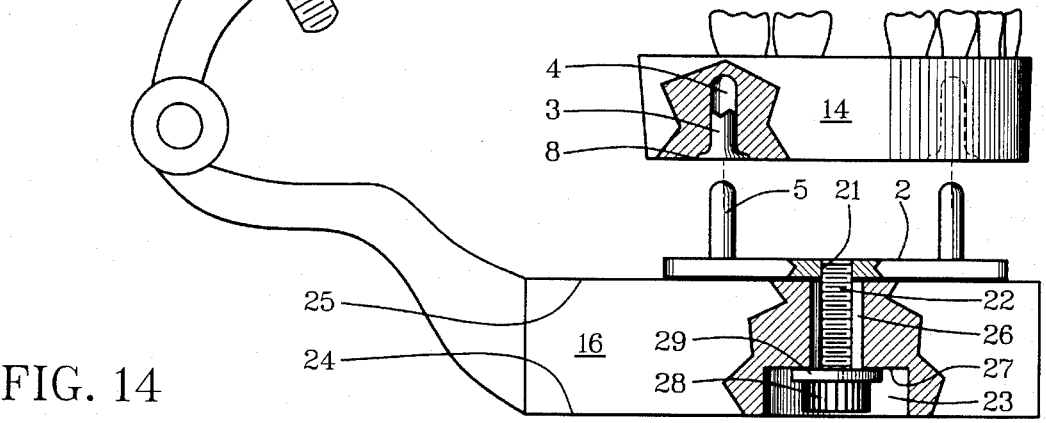
FIG. 14 is a partially cutaway side elevation view of a typical dental articulator having an articulator-attachment bay in which a threaded fastener is in adjustable fastening relationship to an articulator base plate.

Referring to FIGS. 13–14, an optional means for attaching articulator base plates 2 to articulator jaws 16 of dental articulators 15 can be provided with pin shanks 5 that are attached variously to the articulator base plates 2, preferably without either positioning-pin heads 6 or positioning-pin shoulders 7. The articulator base plate 2 is provided with a base-plate fastener orifice 21 that is positioned centrally in the articulator base plate 2 and threaded internally to receive a threaded fastener shank 22. An articulator-attachment bay 23 is extended from a first side 24 of an articulator jaw 16 to a design distance from a second side 25 of the articulator jaw 16. An articulator-fastener orifice 26 is extended from the second side 25 to an internal end 27 of the articulator-attachment bay 23. The articulator-fastener orifice 26 has a cross-sectional area that is designedly larger than a cross-sectional area of the threaded fastener shank 22. The threaded fastener shank 22 has a fastener head 28 with a manual-rotation means such as a knurled exterior as illustrated. A means for preventing the fastener head 28 from entering the articulator-fastener orifice 26 is provided by a large washer 29 and/or a large diameter of the fastener head 28.

A large diameter of the articulator-fastener orifice 26 relative to diameter of the threaded fastener shank 22 allows selective positioning and adjustment of positioning in all directions laterally to an extent desirable for assuring appropriate positioning of the pin shanks 5 on an articulator jaw 16 of a dental articulator 15. The articulator base plate 2 to which the pin shanks 5 are attached can be secured rigidly to the articulator jaw 16 by rotating the threaded fastener shank 22 in the base-plate fastener orifice 21 to cause thread-tightening tension between the second side 25 of the articulator jaw 16 and the internal end 27 of the articulator-attachment bay 23. One or both contact surfaces of the articulator jaw 16 and the articulator base plate 2 can be knurled or otherwise provided with a slip-retardant means.

The FIG. 13–14 means for attachment of the dental model 14 to an articulator jaw 16 of a dental articulator 15 may require the articulator jaws 16 to be constructed of different materials than employed conventionally. Merits of this attachment means, however, justify such a change for desired applications and types of dental articulators 15.

A new and useful pin stabilizer for dental models having been described, all such modifications, adaptations, substitutions of equivalents, combinations of parts, applications and forms thereof as described by the following claims are included in this invention.

I claim:

1. A pin stabilizer for dental models comprising:

a plurality of positioning pins extended perpendicularly from an articulator base plate of a dental articulator;

a plurality of positioning sleeves in a dental model;

one each of the positioning sleeves being sized, shaped and positioned in the dental model to receive one each of the plurality of positioning pins with designed snugness; and wherein the articulator base plate is generally triangular with a generally triangular orifice having internal walls at designed distances inward from outside edges of the articulator base plate.

2. A pin stabilizer for dental models as described in claim 1 and further comprising:

a means for attachment of the positioning pins to the articulator base plate.

3. A pin stabilizer for dental models as described in claim 2 wherein:

the means for attachment of the positioning pins to the articulator base plate has a positioning-pin head on a base end of each of the plurality of positioning pins and a positioning-pin shoulder positioned at a designed distance from the positioning-pin head on each one of the plurality of positioning pins, respectively.

4. A pin stabilizer for dental models as described in claim 1 and further comprising:

a means for attachment of the articulator base plate to desired sizes, types and shapes of the dental articulator.

5. A pin stabilizer for dental models as described in claim 4 wherein:

the means for attachment of the articulator base plate to desired sizes, types and shapes of the dental articulator has at least one base-plate fastener orifice in the articulator base plate and at least one articulator fastener orifice in the desired sizes, types and shapes of the dental articulator; and the at least one base-plate fastener orifice and the at least one articulator fastener orifice are sized, shaped and positioned to receive a fastener shank of at least one fastener member.

6. A pin stabilizer for dental models as described in claim 5 wherein:

the at-least-one base-plate fastener orifice is positioned centrally in the articulator base plate;

the at-least-one base-plate fastener orifice is threaded internally to receive a threaded fastener shank;

an articulator-attachment bay is extended from a first side of an articulator jaw of the dental articulator to a designed distance from a second side of the articulator jaw of the dental articulator;

wherein the at least one articulator-fastener orifice is extended from the second side of the articulator jaw of the dental articulator to an internal end of the articulator-attachment bay;

the at least one articulator-fastener orifice has an inside periphery with a cross-sectional area designedly larger than a cross-sectional area of an outside periphery of the threaded fastener shank;

the threaded fastener shank has a fastener head with a manual-rotation means; and a means for preventing the fastener head from entering the articulator-fastener orifice with the threaded fastener shank being positioned as desired within the at least one articulator-fastener orifice for firmly positioning the articulator base plate selectively on the second side of the articulator jaw of the dental articulator by thread-tightening of the articulator base plate against the second side of the articulator jaw of the dental articulator with fastener tension intermediate the articulator base plate and the internal end of the articulator-attachment bay.

7. A pin stabilizer for dental models as described in claim 1 wherein:

the positioning sleeves are attached to the dental model by means of casting the positioning sleeves in the dental model with the positioning sleeves positioned on the positioning pins.

8. A pin stabilizer for dental models as described in claim 7 and further comprising:

sleeve-retainer members on outside peripheries of the positioning sleeves.

9. A pin stabilizer for dental models as described in claim 7 and further comprising:

at least one locator ring on each of the positioning sleeves respectively.

10. A pin stabilizer for dental models as described in claim 1 wherein:

the plurality of positioning pins are tapered on outside peripheries and the plurality of positioning sleeves are match-tapered on inside peripheries to receive the positioning pins with designed snugness.

11. A method comprising the following steps for construction of a pin stabilizer for dental models:

attaching a desired plurality of positioning pins to an articulator base plate perpendicularly;

positioning a rubber mold on the articulator base plate with the positioning pins inserted through mold orifices in a bottom of the rubber mold;

removably placing a positioning sleeve on each of the positioning pins;

casting at least one dental model in the rubber mold with the positioning sleeves positioned in casting material from which the at least one dental model is cast; and removing the at least one dental model with the plurality of positioning sleeves cast in the at least one dental model from the positioning pins by linear extraction for desired replacement and construction of additional dental models.

12. A method as described in claim 11 and further comprising the additional step of:

attaching the articulator base plate to a desired size, type and shape of dental articulator.

13. A method as described in claim 12 wherein:

the articulator base plate is attached to the desired size, type and shape of dental articulator prior to casting the at least one dental model with the positioning sleeves positioned in casting material from which the at least one dental model is cast.

* * * * *